United States Patent [19]

Sommer et al.

[11] Patent Number: 4,672,120

[45] Date of Patent: Jun. 9, 1987

[54] CHEMICAL AGENTS

[75] Inventors: Harold Z. Sommer, Havre de Grace; George E. Wicks, Jr., Baltimore, both of Md.; Benjamin Witten, Jerusalem, Israel

[73] Assignee: The United States of America as represented by the Secretary of the Army, Washington, D.C.

[21] Appl. No.: 652,651

[22] Filed: Jul. 3, 1967

[51] Int. Cl.[4] .............................................. C07D 401/12

[52] U.S. Cl. ...................................................... 546/261

[58] Field of Search ............... 260/296; 167/46 A, 47; 424/263; 546/261

[56] References Cited

U.S. PATENT DOCUMENTS 3,188,955 6/1955 Brown .................................. 102/24

FOREIGN PATENT DOCUMENTS 782789 9/1957 United Kingdom ................ 260/482

*Primary Examiner*—John F. Terapane
*Assistant Examiner*—John S. Maples
*Attorney, Agent, or Firm*—Anthony T. Lane; Robert P. Gibson; Harold H. Card, Jr.

[57] ABSTRACT

New chemical compounds having the generic formula:

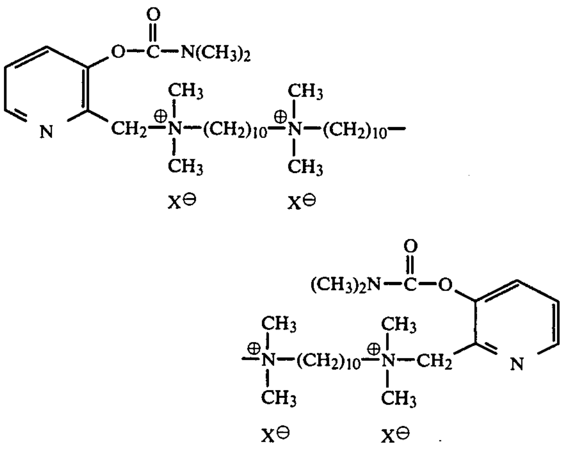

wherein X is one-equivalent of an anion selected from the group consisting of monovalent and polyvalent anions, and having utility as incapacitating agents and in munitions.

3 Claims, No Drawings

CHEMICAL AGENTS

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular junctions. The transmission of impulses along a nerve or from nerve fibers to muscle fibers or secretory cells, or from one nerve fiber to another across synapses in ganglia, is thought to involve chemical changes either directly or as the source of potential differences.

Quaternary ammonium compounds in general are known to be physiologically active materials. Mainly because of their positively charged "onium" centers, they are attracted by anionic sites in animal tissues, particularly those situated at cell surfaces and interfaces. They can induce physiological responses that mimic or antagonized the action of acetylcholine as a result of their interaction with the various physiological receptor sites of acetylcholine, especially those at membranes of muscle cells. They also combine with enzymes such as acetylcholinesterase, other esterases, acetylcholinesacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessability of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures, different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influence association and hydration and may considerably change the solubilities in physiological media. In bis-quaternary and poly-quaternary compounds, the distance between the electric charges must be considered. These factors contribute to governing the rate and reversibility of the chemical reactions involved, which determine the final physiological responses.

Our chemical agents interfere with the normal process of neuromuscular impulse transmission and thus disrupt the propagation of impulses from the nerves to muscles. We have also found these compounds to be extremely toxic at relative low dose levels in various animals.

The object of this invention is to synthesize new lethal agents useful in chemical warfare in high yields wherein said products are well suited for industrial scale manufacture.

Other objects of and uses for the invention will be obvious from the following detailed description.

Our compounds may be employed in any munition suitable for handling a relatively non-volatile toxic agent such as bombs, shells, spray tanks, rockets, missiles, aerosol generators, and others.

In accordance with our invention, 1,10-di(N,N-dimethylamino) decane was quaternized with N-(10-bromodecyl)-N-(3-dimethylcarbamoxy-α-picolinyl)-N,N-dimethylammonium bromide under reflux conditions in a solvent such as acetonitrile. Reflux was maintained for 2 days. The solvent was then evaporated, the oily residue triturated in boiling acetone, and the solvent decanted. The remaining oil was dissolved in acetonitrile and the solution treated with decolorizing charcoal. After the charcoal was removed by filtration, the solution was concentrated and upon adddition of ethyl acetate a precipitate formed which partly solidified after standing at room temperature for 2 days. Total solidification was effected by trituration in ether.

The new compounds of our invention, tetra quaternary ammonium dicarbamates, may be represented by the following generic formula:

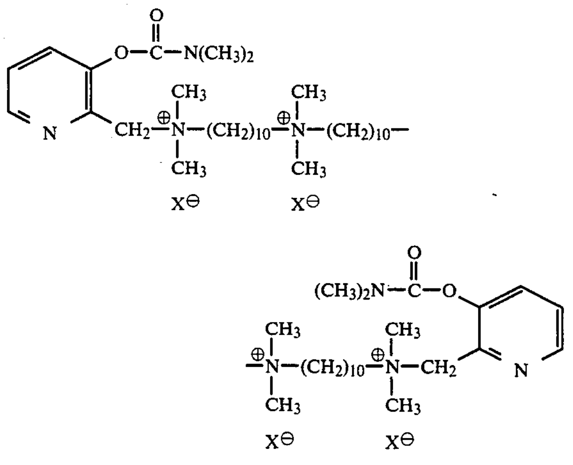

wherein X is one equivalent of a monovalent or polyvalent anion.

The procedure used for the preparation of the new toxic materials is schematically shown as follows:

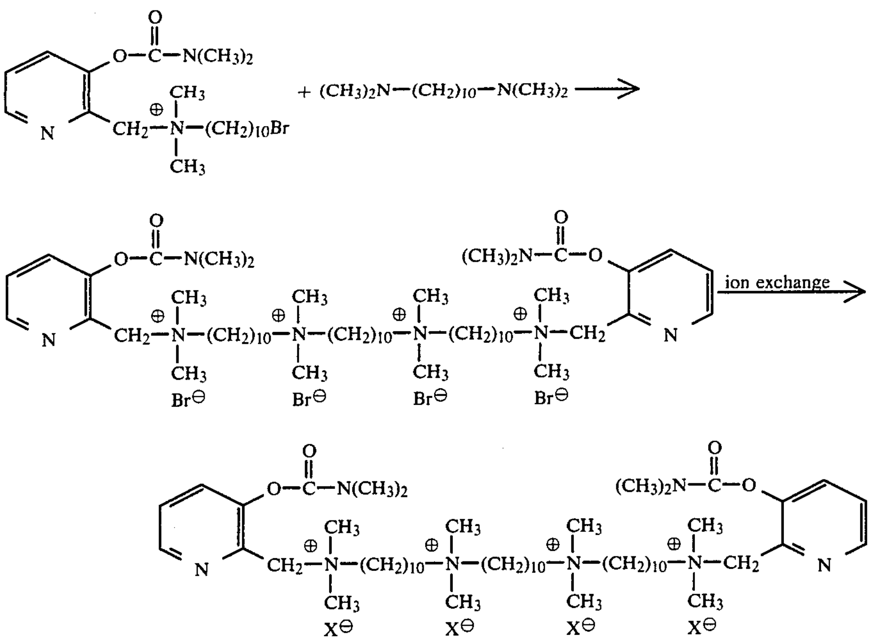

wherein X is a halide anion, preferably bromide.

If compounds are desired in which x is other than a halide ion, the above quaternary compounds are treated with the desired acid by simple exchange reaction as set forth below.

METHOD OF PREPARATION

A solution of 0.5 g of 1,10-di(N,N-dimethylamino)-decane and 3.2 g of N-(10-bromodecyl)-N-(3-dimethylcarbamoxy-α-picolinyl)-N,N-dimethylammonium bromide in 10 ml of acetonitrile was refluxed for 28 hours. The solvent was then evaporated and the oily residue was triturated in boiling acetone. After the acetone was decanted, the remaining gummy material was dissolved in acetonitrile and the solution was boiled with decolorizing charcoal for a few minutes. The charcoal was removed by filtration and the filtrate concentrated at reduced pressure of about 200 mm. Ethyl acetate was then added producing an oily precipitate which partly solidified on standing for 2 days at room temperature. Total solidification was effected by triturating the semisolid in ether. The solid, 2.3 g, was collected on a filter and dried. The resultant hygroscopic material was identified as the tetra (tetraphenylboronate) salt.

IDENTIFICATION OF THE COMPOUND PREPARED

A sample of the above tetrabromide was dissolved in water and this solution was added to an aqueous solution of sodium tetraphenyl boron (in excess). A white solid precipitate immediately formed which was separated by filtration, dried and analyzed. The material, 1,10 Bis{[10-(3-dimethylcarbamoxy-α-picolinyl)methylaminodecyl]methylamino}decane tetrametho(tetraphenylboronate), melted between 72°-80° C. with decomposition.

Analysis of $C_{152}H_{186}B_4N_8O_4$: Calculated: C, 81.8; H, 8.4; N, 5.0. Found: C, 81.7; H, 8.5; N, 5.0.

| Toxicity Intravenous $LD_{50}$ | |
|---|---|
| Rabbits | Mice |
| 0.008 mg/kg | 0.032 mg/kg |

PREPARATION OF INTERMEDIATE TO USE AS STARTING MATERIAL

N-(10-Bromodecyl)-N-(3-dimethylcarbamoxy-2-pryridl-methyl)dimethylammonium Bromide A solution of 62.3 g of 2-dimethylaminomethyl-3-dimethylcarbamoxypyridine and of 251 g of 1,10-dibromodecane was refluxed for 7 days in 1 liter of anhydrous ether. The product that formed was collected on a filter, washed with two 100-ml portions of anhydrous ether, and dissolved in 1 liter of acetone. The acetone solution was treated with decolorizing carbon and filtered. The filtrate was concentrated under reduced pressure to approximately 200 ml. Ether was added until the solution became turbid. The mixture was then seeded and chilled overnight. The resultant crystalline product was collected and further purified by recrystallization from ethyl acetate. The pure product was dried in vacuo for 2 hours, yielding 76 g of material, m.p. 90°-92° C.

Analysis of $C_{21}H_{37}Br_2N_3O_2$: Calculated: C, 48.2; H, 7.1; $Br^-$ (ionic), 15.3, O, 6.1. Found: C, 48.2; H, 7.0; $Br^-$ (ionic), 15.2; O, 6.2.

A representative example of the compounds of our invention which are generically described above is named: 1,10-Bis{[10-(3-dimethylcarbamoxy-α-picolinyl)methylaminodecyl]methylamino} decane tetramethodbromide.

We have shown a preferred compound in which the anion is limited to the halogen moiety, in particular the bromide, since the bromoalkanes are good quaternizing agents. In general, however, it is only necessary that the anions have to meet the requirement of being capable of forming a stable salt with the quaternary nitrogen.

Thus, the halogen ions can be exchanged with other anions of a relatively strong monovalent or polyvalent acid by conventional methods. For example if X is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, hydrogensulfate, nitrate, and tetraphenylboronate. Representative examples of these additional monovalent or polyvalent end products are:

1,10-Bis{[10-(3-dimethylcarbamoxy-α-picolinyl)methylaminodecyl]methylamino} decane tetrametho(hydrogenoxalate).

1,10-Bis{[10-(3-dimethylcarbamoxy-α-picolinyl)methylaminodecyl]methylamino}decane tetramethonitrate.

1,10-Bis{[10-(3-dimethylcarbamoxy-α-picolinyl)methylaminodecyl]methylamino}decane tetrametho(hydrogensulfate).

1,10-Bis{[10-(3-dimethylcarbamoxy-α-picolinyl)methylaminodecyl]methylamino}decane tetramethodperchlorate.

1,10-Bis{[10-(3-dimethylcarbamoxy-α-picolinyl)methylaminodecyl]methylamino}decane tetrametho(tetraphenylboronate).

We claim:

1. New chemical compounds having the generic formula:

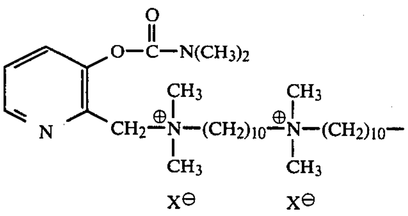

-continued

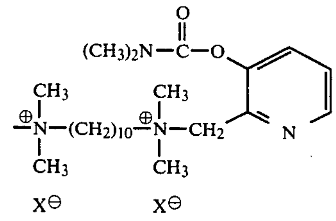

Wherein X is one equivalent of an anion selected from the group consisting of monovalent and polyvalent anions; said anions being selected from the group consisting of halide, hydrogen sulfate, hydrogen oxalate, nitrate, perchlorate, and tetraphenylboronate.

2. A new chemical compound having the name 1,10-Bis{[10-(3-dimethylcarbamoxy-α-picolinyl)methylaminodecyl]methylamino} decane tetramethobromide.

3. A method of producing a new chemical compound having the generic formula:

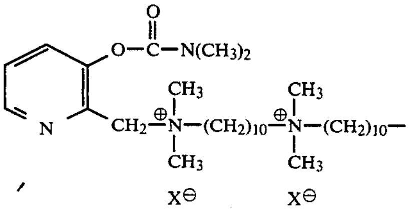

,

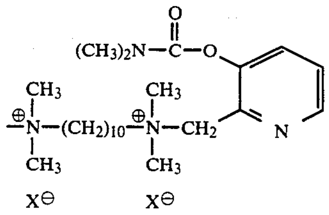

Wherein X is a halide comprising the steps of making a solution of 1,10-di(N,N-dimethylamino decane and N-(10-bromodecyl)-N-(3-dimethylcarbamoxy-α-picolinyl)-N,N-dimethylammonium halide in acetonitrile; refluxing said solution; evaporating the solvent of said solution; triturating the oily residue resulting from said evaporation in boiling acetone; decanting said acetone after said triturating; dissolving the gummy material left after said decanting in acetonitrile; boiling the acetonitrile-gummy material solution with decolorizing charcoal; filtering the acetonitrile-gummy material decolorizing solution; concentrating the filtrate at a reduced pressure; adding ethyl acetate to produce an oily precipitate; allowing to stand at room temperature to partly solidify said precipitate; triturating the semisolid in ether to effect total solidification; filtering the concentrated solution containing the solidified precipitate; and drying said precipitate.

* * * * *